United States Patent [19]

Hill

[11] 4,393,366

[45] Jul. 12, 1983

[54] ROTATING BEAM OCULAR IDENTIFICATION APPARATUS AND METHOD

[75] Inventor: Robert B. Hill, Portland, Oreg.

[73] Assignee: Eye-D Development II Ltd., Portland, Oreg.

[21] Appl. No.: 235,150

[22] Filed: Feb. 17, 1981

[51] Int. Cl.³ .............................. G06K 9/00; A61B 3/10
[52] U.S. Cl. ............................................ 382/2; 350/6.4; 350/6.5; 351/221; 382/65
[58] Field of Search ................... 340/146.3 E, 146.3 F, 340/146.3 AC, 146.3 R; 351/6–9, 14–18, 30, 32, 39; 350/6.3, 6.4, 6.5, 6.9, 6.91

[56] References Cited

U.S. PATENT DOCUMENTS

| | | | |
|---|---|---|---|
| 3,973,836 | 8/1976 | Govignon | 350/6.4 |
| 4,068,932 | 1/1978 | Ohta et al. | 351/7 |
| 4,213,678 | 7/1980 | Pomerantzeff et al. | 351/7 |

*Primary Examiner*—Leo H. Boudreau
*Attorney, Agent, or Firm*—Eugene D. Farley

[57] ABSTRACT

In a method and apparatus for acquiring and recording an identification pattern from the reflectance of the fundus of an eye, a single light source is operable to produce a substantially columnar source beam of infrared light directed into the fixated eye from a plurality of sequential, angularly divergent positions. The light is focused on the retina and reflected in part out of the eye. Variations in the ocular structure contribute to various reflected intensities. The intensity of the reflected light is detected, measured and recorded for each sequential angularly divergent position forming a unique and repeatable identification pattern, or "signature" for each individual.

26 Claims, 17 Drawing Figures

ROTATING BEAM OCULAR IDENTIFICATION APPARATUS AND METHOD

BACKGROUND OF THE INVENTION

This invention relates to apparatus and method for recognizing an individual and/or for verifying an individual's identity. It pertains particularly to such apparatus and method which records for comparison a unique and repeatable electronic identification pattern of an individual's unique ocular structure.

In the current machine-oriented society there is need for a rapid, positive, automatic verification of a person's identification. Prior art methods of verification include photographs, fingerprints, signatures, voice prints, or presentation of an identification number, either by the person or by a magnetic strip on a card.

The first four of these prior methods are not readily adaptable to automatic machine verification as an operator is required to make a subjective comparison. Even if the particular comparison could be made by a machine, it would be time consuming to interpret the data and to make the comparison. Thus, on-the-spot verification would not be feasible.

The use of a number, while capable of automation, poses serious security problems since either the number or the card containing it is subject to loss or theft.

My previous U.S. Pat. No. 4,109,237 discloses a basic method and apparatus for identifying individuals through their retinal vasculature patterns. The apparatus therein discussed includes a plurality of light sources arranged in dual concentric circles. The light sources are sequentially illuminated and darkened, providing a flying spot light source. Green light is used so that it is substantially absorbed by the dark red blood vessels and substantially reflected by the retinal tissue.

However, it has been found that the use of visible light of sufficient intensity to provide a recognizable output signal often causes discomfort to the individual being identified. It also causes the pupil to constrict, making it more difficult to record the scan due to light attenuation caused by the small pupil size.

The present invention overcomes the above disadvantages and is an improvement over that disclosed in my previous patent.

Accordingly, it is the general object of this invention to provide an improved apparatus and method for obtaining and recording an identification pattern from the reflectance from the fundus of an eye.

It is another object to provide in such apparatus a single light source of constant intensity, and optics and to project the light from the source into the eye from various sequential, angularly divergent positions.

It is another object to provide a relatively uncomplicated optical system having few moving parts for recording such an identification pattern.

It is another object to provide an infrared light source which will not affect the pupil dilation during the pattern recording scan.

It is yet another object to provide spacial and spectral filters in the optical path to reduce optical noise.

It is a further object to provide a fixation apparatus to locate the eye repeatedly in the source beam each time the apparatus is used.

It is another object to increase the speed and reliability of comparison.

It is a further object to provide correct optical refraction for each user.

It is a still further object to provide an identification recording apparatus which is safe, easy, and automatic for use without the aid of an operator.

Other objects and advantages of the present invention and the manner in which they are achieved will be made apparent in the following specification and claims.

SUMMARY OF THE INVENTION

In its basic concept the present invention is an apparatus and method for obtaining and recording an identification pattern from the structure of the fundus of an eye. Included in the apparatus is a single light source operable to produce a substantially columnar beam of light, a means for directing at least a portion of the beam into the eye from various sequential, angularly divergent positions, means for detecting the amount of light reflected from the eye at each angularly divergent position, and means for recording the amounts of light thus sensed.

In operation, the person to be identified places his eye in the columnar source beam of light. The beam is directed into the eye from various angularly divergent positions, the light substantially focusing on the retina and being reflected in part out of the eye. The amounts of light thus reflected are sensed and recorded, forming an individual identification pattern.

DESCRIPTION OF THE PREFERRED EMBODIMENTS

The hereindescribed identification apparatus and method takes advantage of the fact that of all human physiological features, the image of the structure of the fundus of the eye is the best identifying characteristic. This is for the reason that each such retinal image is unique to the individual. It is particularly unique in the number of major retinal blood vessels in the area of the optic disk and the relative angles and branching characteristics of these vessels as they emerge from the optic nerve. Further substantially stable features of the fundus of the eye include the size of the optic disk, pigments or coloring patterns of the retina, and the choroidal vasculature.

The retina of the eye is anatomically and physiologically a part of, and an extension of, the brain which nature has provided with the highest precision biofeedback system for environmental control. This remains intact and effective throughout life, even in the presence of bodily trauma, disease and stress.

It is impossible to counterfeit the retinal image. Further, because the identifying characteristic involves the subject's function of seeing, changing the retinal image is impossible. Still further, because of relatively simple optical access, the retinal image is easy to acquire. Focusing of the eye aids in its acquisition. The eye provides much of the optics required to obtain the image.

Also, retinal images are easily susceptible to automated acquisition. No subjective interpretation of the data need be made. The number of variables is small, making the identification process simple and reliable to a machine.

The method of the present invention broadly comprises digital acquisition of the reflectance pattern of the back inside of the eye for the purpose of providing the data by which a digital computer can identify individuals.

More particularly, the method for obtaining the pattern comprises first causing the person's eye to become fixated and positioned by fixation and positioning means. Preferably the eye is indexed relative to a fixation target and positioned both horizontally and vertically to a precise degree and axially to a less precise degree relative to the cornea of the eye being scanned. This procedure causes a particular section of the eye to be presented in order to obtain a repeatable pattern and assures that the entire scan beam enters the pupil.

Once the eye is fixated and positioned, it is scanned with an infrared light source which is arranged in a selected pattern determined efficiently to intercept the major contrasting features. These features are largely comprised of the major vessels and especially the veins contrasted with the surrounding tissue. The reflected portion of the light is detected, filtered, converted to digital form, stored in computer memory and sent to a host computer as reference data or to be matched with reference data acquired earlier.

Figure 1:
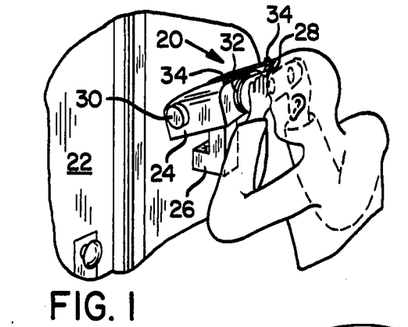
FIG. 1 is a fragmentary pictorial perspective view of an individual using the identification apparatus of the present invention.

As shown in FIG. 1, the identification apparatus of my invention, shown generally at 20, is mounted in an easily accessible location at an identification check point, for instance a funds transfer machine or a security entrance, as illustrated at 22. It comprises a case 24, which encloses the hereinafter described optics, and a mounting bracket 26 which supports the apparatus at a convenient position for the user. Preferably a head bracing means such as a light shield or head support 28 is provided to position the user correctly for looking into the instrument. A knob 30 controls the interpupillary distance and another dial or lens turret 32 controls focus. A trigger or button 34 is operable by the user to initiate the identification sequence.

Figure 2:
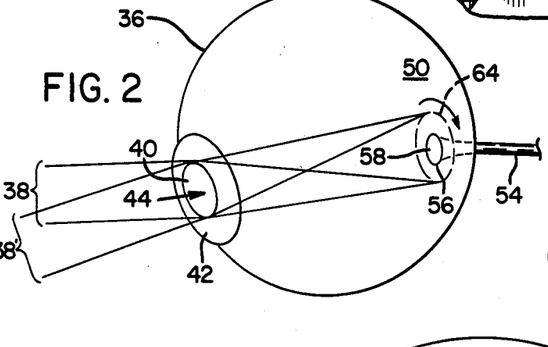
FIG. 2 is a diagrammatic side perspective view of an eye showing sequential positions of rays entering therein.
Figure 3:
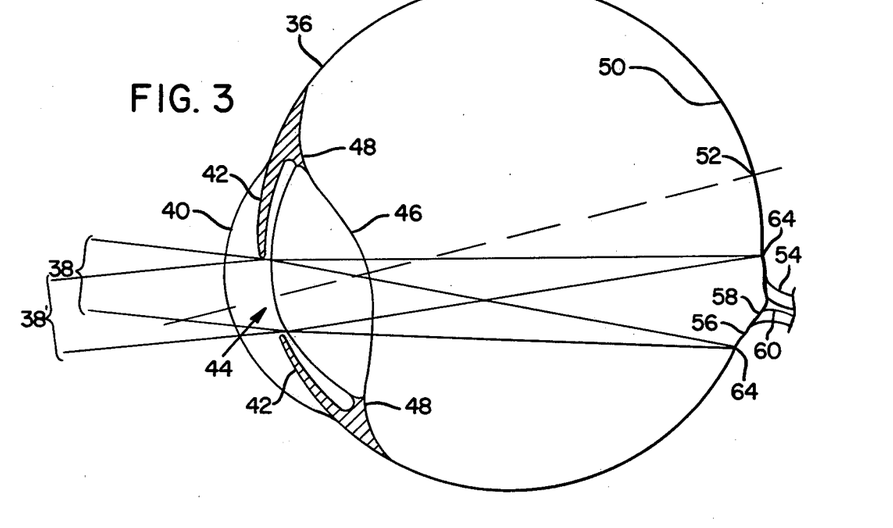
FIG. 3 is a diagrammatic plan view of the right eye showing the refraction of rays entering therein.

FIGS. 2 and 3 show a diagrammatic representation of an eyeball 36 having beams 38 and 38' entering therein. The anterior portion of the eye includes a cornea 40, and behind the cornea an iris 42 having a pupil 44 as its central opening. A lens 46 is located behind the iris supported by muscles 48 which, by expanding or contracting, may vary the focus of the lens.

The posterior or fundus portion of eyeball 36 includes a retina 50, which is the light sensitive tissue of the eye, and other supporting structures. The most light sensitive portion of the retina is the fovea 52 which is directly on the axis of the eye and is very densely packed with the light receptor structures, i.e. the rods and cones (not shown).

The nerves from retina 50 exit eyeball 36 through an optic nerve 54 which is approximately 15.5 degrees off axis toward the inside, or nasal side of the eye. The area of the retina where the optic nerve attaches, i.e. the optic disk 56, is substantially void of light receptor structures, thus forming the "blind spot" of the eye. In the central portion of the optic disk is a slight depression or cup 58.

Figure 6:
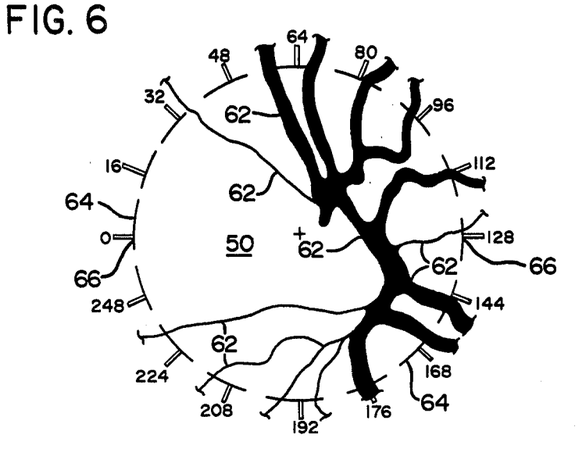
FIG. 6 is a diagrammatic view of a circular scale used in the method of identification of the present invention, superimposed on a representation of the retinal vasculature of an eye.

A pair of blood vessels 60 centrally located in optic nerve 54 supply blood to and drain blood from retina 50. As best shown in FIG. 6, these vessels branch in the retina to form a vascular network 62. This vasculature is visible upon looking into the eye and appears as dark or non-reflective lines on an otherwise more reflective retina.

The central blood vessels 60 need not enter at exactly the center of optic disk 56, as is evident in FIG. 6. However, upon entry the blood vessels rapidly branch into a plurality of smaller vessels which extend somewhat randomly throughout the retina. Generally, no large blood vessels are found in the area of fovea 52 which is off the left side of the drawing of FIG. 6. This retinal vasculature is a very stable congenital structure and is unique to each individual, providing a definitive identification pattern.

Other structures (not shown), for example pigmentation, variations in the density of rods and cones, and the vasculature of the choroid, may also be observable in the use of the present invention. They also are substantially stable and contribute to a unique identification pattern. For purposes of simplifying terminology, however, all such structures will herein be referred to as the retinal vasculature, ocular vasculature, or as tending to vary the reflectance from the fundus of the eye.

FIGS. 2 and 3 show a columnated beam of light 38 directed into the eye. The eye is focused on infinity, and thus all rays in the column are focused to a small spot on retina 50. The entering beam is operable to move in a cone having its apex at the lens of the eye, and thus enters the eye from a circle of sequential angularly divergent positions such as is shown at 38'. Thus a locus of points is illuminated on the retina, as is illustrated by the dashed circle 64.

Figure 4:
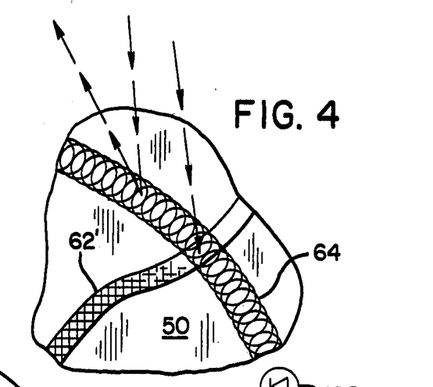
FIG. 4 is a fragmentary detailed plan view of a portion of the retina which is utilized in the identification.

FIG. 4 is an enlarged view of retina 50 showing a segment of the locus 64. One of the blood vessels 62' extends across this area of the retina and is intersected by the locus of sequentially illuminated points. As shown by the arrows, light striking the retina is reflected, while light striking the darker blood vessel is substantially absorbed.

Figure 7:
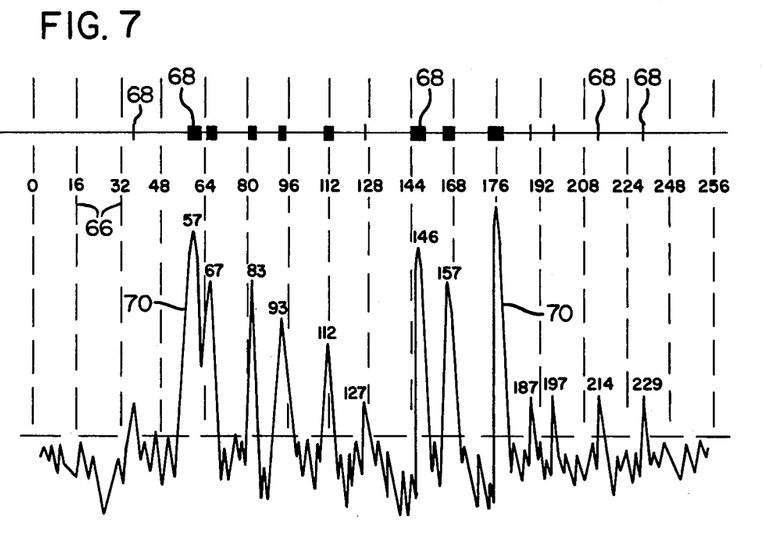
FIG. 7 is a linear diagrammatic view of the scale of FIG. 6 showing the intercept points of the blood vessels with the scale and a graph of the absorption of light along the path defined by the scale.

Now referring to FIGS. 6 and 7, a circular scale, shown at 66, is used in the practice of my invention. The circular scale is graduated in 256 divisions, each representing a location where the intensity of light reflected back from the fundus of the eye is measured. Locus 64 conforms to the dashed circle, and in FIG. 7 a dark bar 68 is shown where the reflected intensity is low due to absorption of the light by a blood vessel. A graph 70 illustrates the absorption as smoothed over the 256 points. Some background noise is evident in the measured intensities. However, major changes in the reflected intensity are a result of readily observable structures in the eye.

Figure 8:
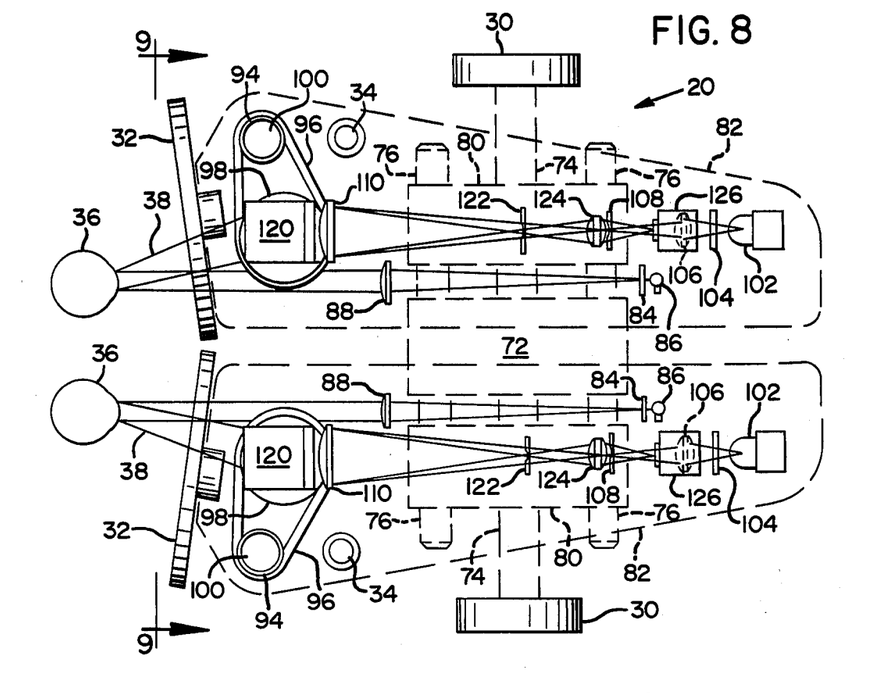
FIG. 8 is a top view of a first embodiment of apparatus of the present invention.
Figure 9:
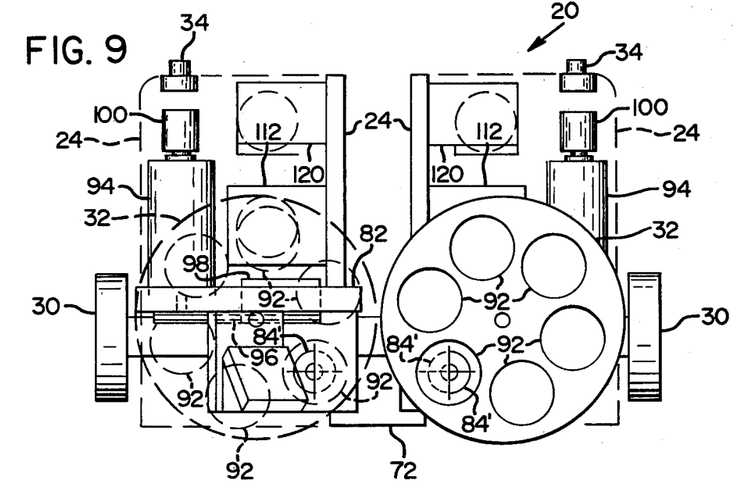
FIG. 9 is a front view of the apparatus of FIG. 8, looking in the direction of arrows 9—9 in FIG. 8.

The apparatus of the present invention is shown in a first embodiment in FIGS. 8 and 9. While the scanning of a single eye is adequate for purposes of obtaining a unique identification pattern, the apparatus is preferably binocular, as illustrated. This aids particularly in repeatably stabilizing the orientation and fixation of the eyes, as well as allowing use by individuals who can see only in one eye.

FIG. 8 shows a top view of the apparatus, including two halves which are essentially inverse duplicates of each other. The apparatus is mounted on a center pedestal 72 attached to mounting bracket 26 and through which extends an interpupillary adjustment screw 74 and a pair of guide pins 76. Adjustment knobs 30 are attached to the ends of the adjustment screw.

Screw blocks 80 are threaded on the adjustment screw, one with a right hand thread and one with a left hand thread so that they will move inwardly or outwardly together as the adjustment screw is turned. Each screw block is fixed to a plate 82 which in turn mounts the hereinafter described optics. Interpupillary adjustment screw 74 thus provides a means operable to adjust the distance between the beams to accommodate various users.

The fixation optics includes, for each eye, a fixation reticle 84, illuminating means for illuminating the fixation reticle, preferably a light emitting diode 86, and a columnating means 88 for columnating the light from the light-emitting diode.

The fixation reticles each include a pattern. Although the reticles may have an identical appearance, preferably a complete crosshair pattern, the patterns illustrated in FIG. 9 are complementary, wherein one reticles pattern is one half of a crosshair pattern 84' and the other reticle pattern is the other half of the crosshair pattern 84'.

Drive current to the fixation light-emitting diodes is alternated so that both are not on at the same time. The reason for this is to prevent one eye's perception from dominating the other, especially when the discs do not fuse. When the interpupillary distance is correct and the head is positioned properly the reticle images will fuse and the crosshair will be centered in the illuminator beam.

Each eye 36 can focus straight ahead on the images 84' of the fixation reticles. Because the light is columnated, the images appear at infinity, and because the beams are parallel the eyes assume a naturally relaxed position.

As shown best in FIG. 9, a pair of lens turrets 32 is mounted on the front of the identification apparatus for individual adjustment by each user. Each lens turret houses a plurality of refraction correction lenses 92. Each lens in each turret has a different refractive power so a wide range of corrections is available. As best shown in FIG. 8, the turrets are mounted at an angle with respect to the fixation axis, the purpose of which will be discussed hereinafter.

FIGS. 8 and 9 also illustrate, in each half of the apparatus, a motor 94 which drives a belt 96 which in turn rotates a prism journal 98. An encoder 100 is attached to the motor for determining its rotational position and consequently the rotational position of the prism journal.

Figure 10:
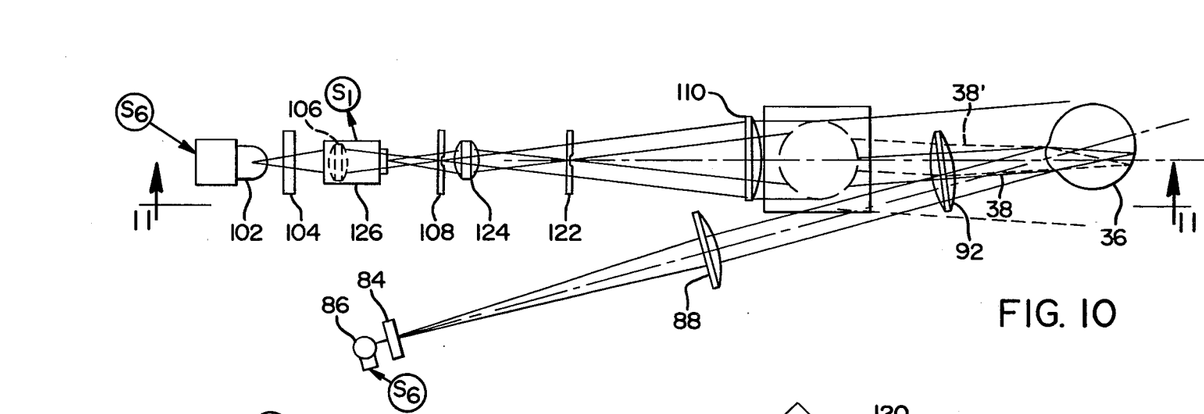
FIG. 10 is a schematic plan view of the optics of the apparatus of FIG. 8.
Figure 11:
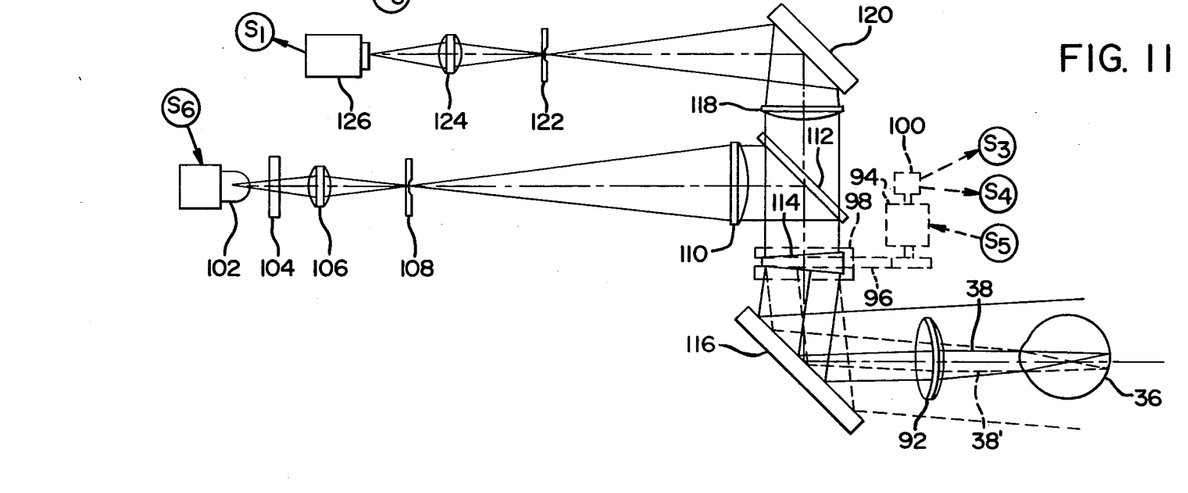
FIG. 11 is a schematic side view of the optics of FIG. 10 looking in the direction of arrows 11—11 in FIG. 10.

The beam directing optics of the present invention for driving beam 38 in a substantially circular or conical pattern, as discussed above, are best shown in a first embodiment in FIGS. 10 and 11.

FIG. 11 shows the beam rotating components of the system. A light source, preferably an incandescent tungsten filament 102, produces a broad spectrum of light, part of which is in the near infrared range from 7500 to 9500 Angstrom units of wavelength. An infrared filter 104 allows only this infrared radiation to pass further into the system. A lens 106 then focuses the light through a source pinhole 108 which intercepts all unwanted rays and leaves only a clearly defined spot to be transmitted into a columnating lens 110. The resultant column of light is then reflected off of a partially silvered mirror 112 and through a rotating prism 114 mounted in prism journal 98. The beam is then reflected by mirror 116 through one of lenses 92 in lens turret 32 and into the user's eyeball 36.

As the beam passes through rotating prism 114 it is deflected a small amount, preferably about 4.5 degrees. Thus, as the prism rotates, the resultant beam describes an outwardly divergent cone. However, the diverging beams coincide for some distance and form an inner cone having its apex spaced apart from the prism. The rays passing through this apex come through a single spot on the outside edge of the prism. As the prism is rotated, so also is this spot.

As shown, the eyeball 36 of the user is presented in this inner cone of coincident beams at such a point that the size of a section of the cone substantially coincides with the size of pupil 44. Thus a single spot on the perimeter of the prism is responsible for refracting light into the eye from a plurality of sequential, angularly divergent positions. The remainder of the rotating prism may be blackened to eliminate the peripheral light which would be directed onto the white of the eyeball and the face of the user if the prism were all transparent. The diverging rays in the beams are illustrated for purposes of explanation only.

Before passing through lens 92 the beams of light are columnar. However, since some users are not able to focus their eyes at infinity, a means for correcting the user's vision, such as refraction lens 92, is required. Preferably the user does not wear spectacles when using this apparatus since they would induce refractive variation as a result of variation in spectacle/corneal orientation, and would tend to cause unwanted reflections. However, similar restrictions do not apply to contact lenses since they mold to cornea 40. Lens 92 varies the beam from columnar a slight amount so that the beam will be focused on the retina and thus provide vision correction.

At any one time the small spot on retina 50 upon which the light strikes then reflects a portion of the light randomly back into the interior of eyeball 36. The reflected intensity depends on the type of structure encountered. The rods and cones tend to be quite reflective, while blood vessels 62 absorb much of the incident light.

Part of the reflected light is directed toward lens 46 of the eye. This light then follows the reverse path of incoming source beam 38. It is columnated by the lens of the eye to form a reflected beam coincident with the source beam and then travels through corrector lens 92, reflects off mirror 116, and is bent slightly back to a parallel optical axis as it passes through prism 114. A portion of the reflected beam is transmitted through partially silvered mirror 112 and is thus separated from the source beam.

The separated portion of the reflected beam is then focused by a focusing lens 118, reflected by a mirror 120 and directed through a receiver pinhole 122. The pinhole blocks stray light which might originate from reflections from surfaces other than the illuminated spot in the eye. Thereafter, the light is refocused by a lens 124 onto a detector 126. The detector senses the amount or intensity of light in the reflected beam.

FIG. 10 illustrates the relationship between the main or scanner optical axis and the fixation optical axis. The fixation optics are mounted at between 14 and 17 degrees, and preferably at approximately 15.5 degrees from the scanner optical axis or the axis around which the source beam is angularly divergent. Eyeball 36 is oriented so that the image of fixation reticle 84 is focused at fovea 52. Thus, the source beam enters the eye obliquely with the scanner axis intersecting the center of optic disk 56. Lens 92 is oriented to bisect the angle between the fixation axis and the scanner axis so that both beams encounter similar refraction in the lens and reflections from the surfaces of the lens do not create unwanted optical noise.

Figure 12:
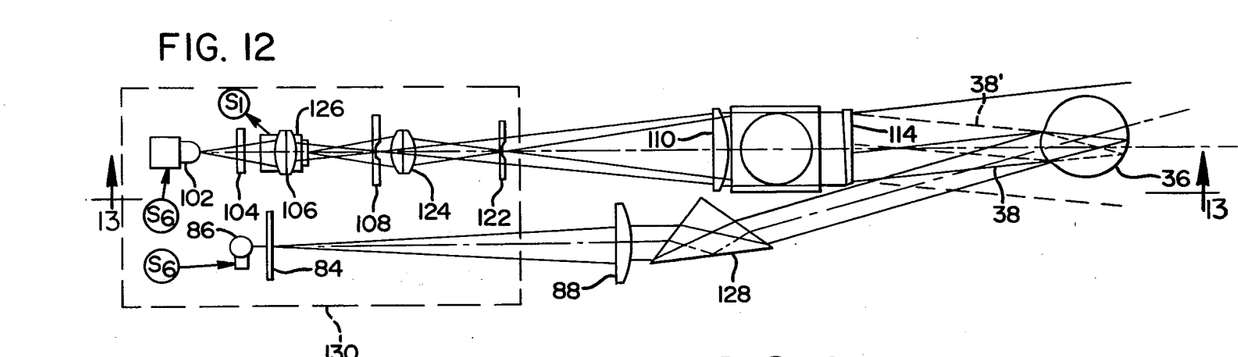
FIG. 12 is a schematic plan view of a second embodiment of the optics.
Figure 13:
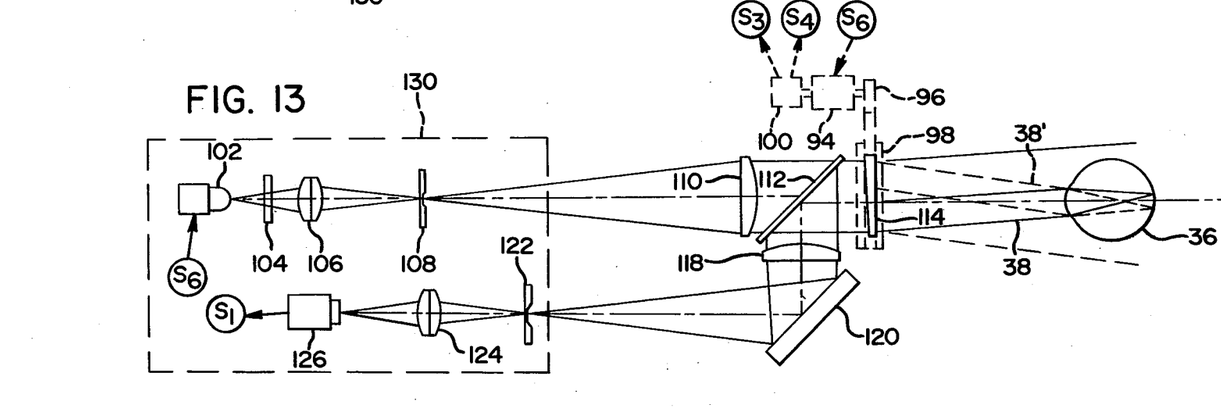
FIG. 13 is a schematic side view of the optics of FIG. 12 looking in the direction of arrows 13—13 in FIG. 12.

FIGS. 12 and 13 illustrate a second embodiment of the optics of the present invention. The components of the system are substantially the same, with the exception of the apparatus and manner of compensating for refraction correction for various users. This correction is accomplished without the need for a refraction lens 92 as previously described.

The fixation beam is reflected by a prism 128 so that the initial fixation axis is parallel to the scanner axis. The fixation reticle 84 and source 86, as well as scanner source 102, filter 104, lens 106 and pinhole 108, and the detector 126, lens 124, and pinhole 122 are all mounted on a carriage 130. The carriage is operable to move back and forth parallel to the optical axes.

It should be noted that the distance between reticle 84 and lens 88 is the same as the distance between pinhole 122 and lens 118, and pinhole 108 and lens 110. Thus, when the carriage is positioned at other than the focal length of the lenses the resultant beam is not columnated, but varies slightly from columnar at the right amount to correct the vision of the user. Further, as the user fixates on the fixation pattern, adjusting the carriage so that the pattern is in focus also focuses the scanner optics.

Figure 14:
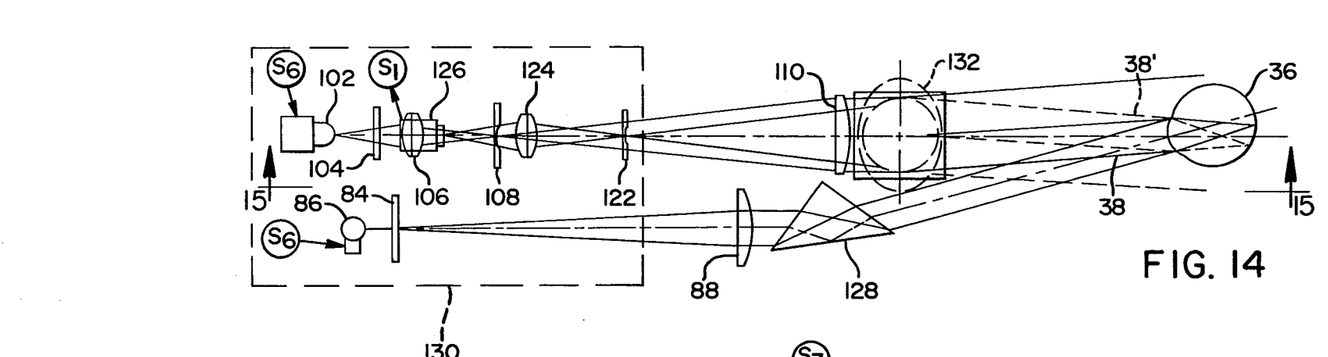
FIG. 14 is a schematic plan view of a third embodiment of the optics.
Figure 15:
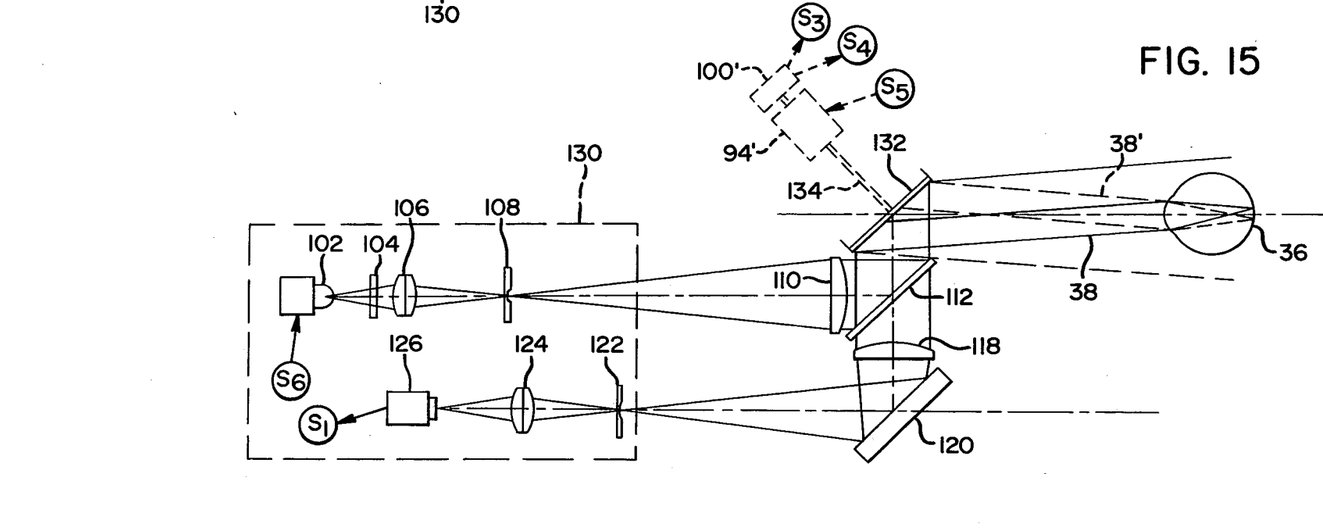
FIG. 15 is a schematic side view of the optics of FIG. 14 looking in the direction of arrows 15—15 in FIG. 14.

FIGS. 14 and 15 illustrate a third embodiment of the optics of the present invention. In this embodiment the beam directing means comprises a rotating mirror 132 mounted in the light path in place of rotating prism 114. The mirror is mounted on a shaft 134 and rotated by motor 94'. The mirror is not normal to the shaft, rather it is preferably tilted approximately 2.25 degrees from normal. This will cause the light to be reflected in an outwardly diverging cone as the mirror is rotated.

Similar to the embodiment having the prism, the diverging reflected beams coincide for some distance forming an inner cone having its apex spaced apart from the rotating mirror. And, as with the prism, only a single spot on the mirror is utilized in reflecting the source beam 38 into the eye. The remainder of the mirror may be blackened to prevent unwanted reflections. A shaft encoder 100' is attached to motor 94' to determine the rotational position of the motor and thus the direction of the beam of light 38 reflected from the mirror.

The use of rotating mirror 132 in fact does not produce an exact circle of reflected beams. Because it is at an angle with respect to the incident beam, it rather produces an oval pattern. However, this pattern is constant or reproducible from use to use, so no error is introduced by it.

Figure 5:
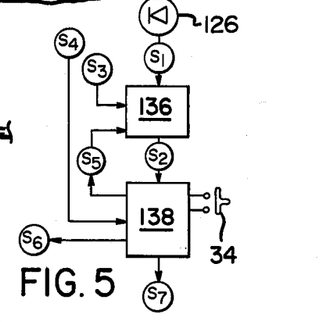
FIG. 5 is a schematic representation of the electronics of the apparatus of the present invention.

FIG. 5 illustrates, in schematic form, the electronics of the present invention. Detector/amplifier 126 produces an electric analog signal $S_1$ corresponding to the intensity of light striking the detector. An analog to digtal converter 136 receives this signal and produces a digital output data signal $S_2$ corresponding to the analog input signal. Signals $S_3$ and $S_4$ are produced by encoder 100. Signal $S_3$ is a strobe signal, pulsing once for each of the 256 positions shown by scale 66. Signal $S_4$ is a start strobe, pulsing once at a point corresponding to the zero point on the scale.

A digital computer 138 receives the signals $S_2$ from the converter 136, and $S_4$ from the encoder 100. A return start or "on" signal $S_5$ is produced by the computer and is directed to the converter. Also, the computer produces an on/off signal $S_6$ to control light sources 86 and 102 and motor 94. The final output is electric signal $S_7$.

OPERATION

The individual user wishing, for example, to gain access to a particular security area presses the start button 34 of the identification apparatus to activate the scanner motor and scanner lamp. The user now adjusts focus for each eye by manipulating lens turrets 32.

When the user first uses the apparatus, the corrector setting for each eye is accomplished in the following manner: He sets one turret to occlude the fixation target for its corresponding eye and sets the other turret for its most far sighted (positive diopter) correction. If the fixation target presented to the non-occluded eye is out of focus, he starts to step the turret for that eye toward the most near sighted position (most negative diopter). When the target first comes into focus, he stops stepping the turret and notes the number appearing on the turret for that eye. He then repeats this procedure for the other eye.

The user now adjusts the interpupilary distance by manipulating knob 30 to achieve the appropriate distance between the two fixation optics axes. The user adjusts the distance between the device eyepieces to match his interpupillary distance. When the user first uses the apparatus, this adjustment is made in the following manner: The user peers into the device and adjusts the inter-pupillary knob 30 until the two defocused images are intersected by the vertical line of the reticles 84. The user notes the calibration number appearing on the knob 30 and thereafter simply sets the appropriate pupil-distance number before peering into the apparatus.

The user tilts his head until the defocused red half discs are adjacent, forming what appears to be a single defocused disc illuminating the crosshair reticle image.

The user now initiates the scan sequence by pressing scan button 34. Digital computer 138, by signal $S_6$ turns on motor 94 and scanner light source 102. The motor is given adequate time to achieve the proper speed, then the scan sequence is initiated.

The encoder start or zero signal $S_4$ pulses once per complete revolution of scanning beam 38. Preferably the start signal is coordinated with the beam focusing on the side of the scan locus closest to fovea 52. This area is the least likely to have major blood vessels and consequently the encounters with most of the light-absorbing structures will be centrally located in the scan sequence.

The computer 138, upon receiving the start signal $S_4$ from encoder 100, produces a start or "on" signal $S_5$ which instructs converter 136 to begin sending digital data $S_2$ to the computer. The encoder generates a strobe signal $S_3$, pulsing once for each data point to be sampled. On each pulse the converter converts the instantaneous analog voltage $S_1$ to a digital equivalent and sends it to the computer. This occurs in rapid succession for each of the 256 points. Then the encoder pulses signal $S_4$ again, terminating the data stream. In the binocular version of the apparatus a similar procedure is either simultaneously or sequentially carried out for the other eye, and the two patterns thus obtained are combined into a single identification pattern.

It should be remembered that the data are originally obtained from the reflectance from a plurality of sequentially divergent positions from the fundus of the eye. Consequently, by repeating the scanning cycle, optical and electrical noise may be filtered out while enforcing the good signal which is the varied reflectance. Computer 138, having recorded the data, is thus able to analyze it and determine if repeating the scan would significantly increase reliability. If so, another scan is taken. This entire process occurs so quickly that the user is unaware of the complex operations being performed.

Of course, in the most basic form of the invention, any means to record the various initial intensities of the scan is all that is required. However, the use of modern digital computers for controlling the process increases the speed and reliability of the system.

After the scan is completed, computer 138, via on/off signal $S_6$, turns off motor 94 and light sources 86 and 102. The identification pattern thus recorded is output via signal $S_7$.

Thereafter the user's identification pattern may be compared with a reference pattern or a plurality of reference patterns to determine or verify the identity of the user. This comparison process may best be performed by programmed general purpose digital computers having mass storage containing the recorded identification patterns of many users.

Initially, for the identification system to be used, the ocular vasculature patterns of all individuals of known identity authorized to use the system need to be entered into the data storage area. This involves an initial registration of each user in which the pattern is merely recorded, becoming the reference pattern for later recall and use.

Figure 16:
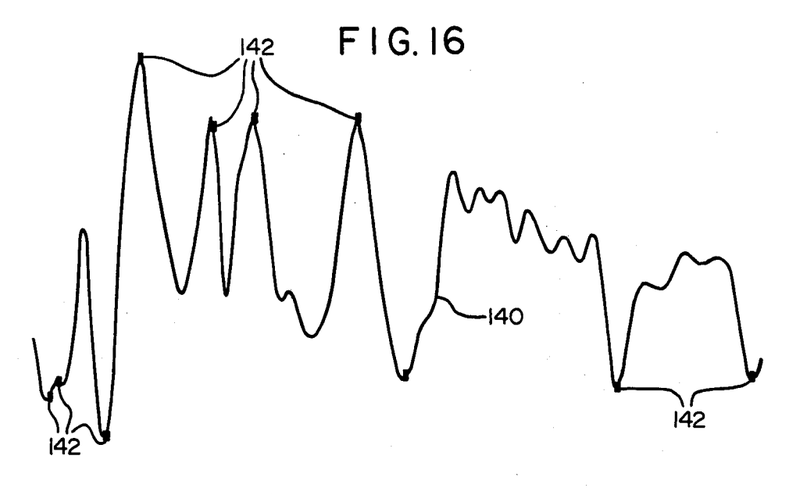
FIG. 16 is a waveform representing the retinal pattern of one individual, the rectangles identifying major maximum and minimum intensity points of the waveform.
Figure 17:
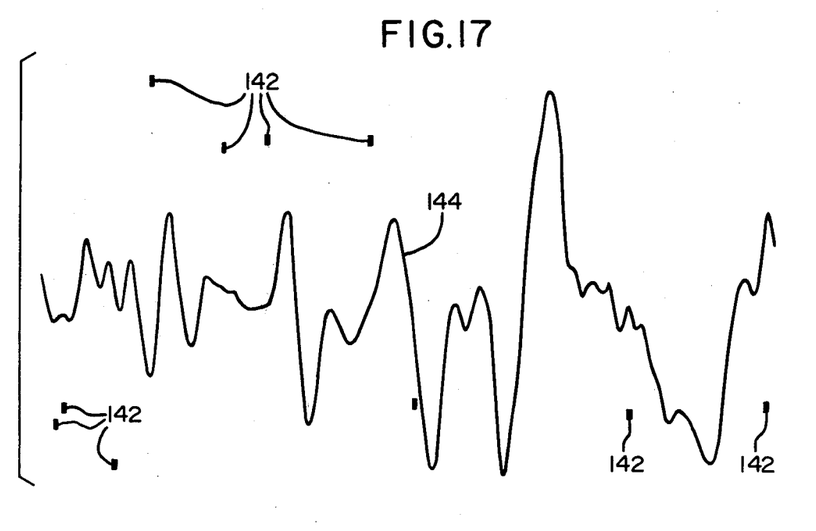
FIG. 17 is a waveform representing the retinal pattern of a second individual with the identifying rectangles of FIG. 16 associated therewith to show the mismatch of the waveforms and thus prove the difference between the individuals.

FIG. 16 illustrates the waveform 140 representing the retinal pattern of an eye of one individual, with the rectangles 142 identifying ten major maximum and minimum intensity points of the waveform. These rectangles are also shown in FIG. 17 in association with the waveform 144 representing the retinal pattern of an eye of a different individual. It is to be noted that the rectangles 142 do not register with any major maximum or minimum intensity points of the waveform 144. Accordingly, it is apparent that the waveforms 140 and 144 represent the retinal patterns of totally different eyes.

The individuality of the ocular vasculature is such that it is possible, using the present invention, to distinguish each and every sighted person on the earth.

Having described the preferred embodiments of my invention, I claim:

1. Apparatus for recording an identification pattern from the fundus of an eye, comprising:
    (a) a light source operable to produce a substantially columnar source beam of light;
    (b) beam directing means for directing at least a portion of the source beam into the eye from a plurality of sequential angularly divergent positions, the light substantially focusing on the fundus of the eye and being reflected in part out of the eye forming a reflected beam;
    (c) detector means for sequentially sensing the amount of light in the reflected beam at each angularly divergent position of the source beam; and
    (d) means for recording the amounts of light thus sensed to form an identification pattern.

2. The apparatus of claim 1 wherein the light from the light source consists essentially of infrared radiation.

3. The apparatus of claim 1 further comprising a light filter disposed in the source beam of light operable to pass substantially only infrared radiation.

4. The apparatus of claim 1 wherein the beam directing means comprises a prism disposed in the source beam operable to deflect at least a portion of the source beam to direct it into the eye, and motive means operable to rotate the prism so that the portion of the source beam entering the eye comes from various angularly divergent positions as the prism is rotated.

5. The apparatus of claim 4 further comprising an encoder attached to the motive means for determining the rotational position of the prism, and electrical means for associating the instantaneous rotational position of the prism and the instantaneous amount of light in the reflected beam.

6. The apparatus of claim 1 wherein the beam directing means comprises a mirror disposed in the source beam operable to direct a portion of the source beam into the eye, and a motor having its shaft attached to the mirror in non-perpendicular relation and operable to rotate the mirror so that the portion of the source beam entering the eye comes from various angularly divergent positions as the mirror is rotated.

7. The apparatus of claim 6 further comprising an encoder attached to the shaft of the motor for determining the rotational position of the mirror, and electrical means for associating the instantaneous rotational position of the mirror and the instantaneous amount of light in the reflected beam.

8. The apparatus of claim 1 further comprising a beam splitter located in the paths of the source and reflected beams allowing a part of one beam to pass therethrough and allowing a part of the other beam to be reflected therefrom, thereby providing for coincident beams entering and exiting the eye.

9. The apparatus of claim 1 further comprising alignment means for aligning the eye so that the light from the source beam is focused on the fundus of the eye in a pattern substantially centering on the optic disc.

10. The apparatus of claim 1 further comprising vision correction means to slightly vary the columnar nature of the source and reflected beams to provide for vision correction for each of various users.

11. The apparatus of claim 1 further comprising refraction means in the source and reflected beams to refract the light to provide for vision correction for the user.

12. The apparatus of claim 1 further comprising vision fixation means providing a fixation point, illumination means for illuminating the fixation point, and columnating means for columnating the light from the fixation point whereby the fixation point is caused to appear at infinity, the fixation point being observable when the eye is positioned in the source beam of light.

13. The apparatus of claim 12 wherein the column of light from the fixation point is arranged to intersect an axis around which the source beam is angularly divergent, at an angle of between 14 and 17 degrees.

14. Apparatus for recording an identification pattern from both eyes, comprising a dual set of the apparatus of claim 1, the source beam from one apparatus directed into one eye and the source beam from the other apparatus directed into the other eye, and means for combining the two identification patterns thus recorded into a single identification pattern.

15. A method of recording an identification pattern from the fundus of an eye, comprising:
(a) directing at least a portion of a substantially columnar source beam of light into the eye from a plurality of sequential angularly divergent positions, the light focusing on the fundus and being reflected in part out of the eye forming a reflected beam;
(b) sensing the amount of light in the reflected beam at each angularly divergent position of the source beam; and
(c) recording the amounts of light thus sensed to form an identification pattern.

16. The method of claim 15 further comprising the step of aligning the eye so that the light from the source beam is focused on the fundus of the eye in a pattern substantially centering on the optic disk.

17. The method of claim 15 further comprising the step of bracing the head of the user to prevent movement thereof.

18. The method of claim 15 further comprising the step of refracting the beams to provide for vision correction for the user.

19. A method of recording an identification pattern from both eyes comprising repeating the steps of claim 15 for each eye and combining the two identification patterns thus obtained into a single identification pattern.

20. An apparatus for repeatably stabilizing the orientation and fixation of the human eyes, comprising:
(a) a first fixation reticle providing a first fixation point;
(b) illuminating means for illuminating the first fixation reticle;
(c) columnating means for columnating the light from the first fixation reticle whereby the first fixation point is caused to appear at infinity;
(d) a second fixation reticle providing a second fixation point;
(e) illuminating means for illuminating the second fixation reticle; and
(f) columnating means for columnating the light from the second fixation reticle whereby the second fixation point is caused to appear at infinity; the columns of light being substantially parallel and spaced apart substantially an interpupillary distance.

21. The apparatus of claim 20 further comprising bracing means for bracing the head of the user to prevent movement thereof.

22. The apparatus of claim 20 wherein the reticles have an identical appearance.

23. The apparatus of claim 20 wherein the reticles comprise crosshair patterns.

24. The apparatus of claim 20 wherein the pattern of one reticle is one half of a crosshair pattern and the pattern of the other reticle is the other half of the crosshair pattern.

25. The apparatus of claim 20 further comprising refraction means in the columns of light to refract the light to provide for vision correction for the user.

26. The apparatus of claim 20 further comprising interpupillary distance varying means to vary the distance between the columns of light to accommodate various users.

* * * * *